United States Patent [19]

Brault et al.

[11] 4,150,298

[45] Apr. 17, 1979

[54] APPARATUS FOR STORING AND EJECTING RADIOACTIVE SOURCES USED IN RADIOTHERAPY

[75] Inventors: Georges Brault; Jacques Blanche, both of Buc, France

[73] Assignee: CGR-MeV, Buc, France

[21] Appl. No.: 788,758

[22] Filed: Apr. 19, 1977

[30] Foreign Application Priority Data

Apr. 20, 1976 [FR] France ............................... 76 11597

[51] Int. Cl.² ............................................... G21F 5/02
[52] U.S. Cl. ...................................... 250/497; 250/507
[58] Field of Search ............................... 250/497, 507

[56] References Cited

U.S. PATENT DOCUMENTS

| 2,916,628 | 12/1959 | Prest | 250/497 |
| 3,593,594 | 7/1971 | Perry | 250/497 |

*Primary Examiner*—Harold A. Dixon
*Attorney, Agent, or Firm*—Karl F. Ross

[57] ABSTRACT

An apparatus used for radiotherapeutic purposes, designed to store a number of radioactive-source carriers and to facilitate their selective ejection via respective sheaths to remote applicators designed to contact anatomical parts to be treated, comprises a cylindrical body inside a metallic enclosure, the body being formed with a plurality of axially extending cylindrical cavities each adapted to accommodate a source carrier. Certain of these cavities, referred to as active, are open at both ends and are connected via respective conduits with associated entrance and exit connectors on the outer surface of the enclosure, the exit connectors being engageable by the ejection sheaths. The remaining cavities, serving for the storage of source carriers, communicate by way of other conduits with ancillary connectors, also on the outer enclosure surface, that can be linked by a transfer tube to the exit connector of a selected active cavity which is to be loaded with a source carrier or from which such a carrier is to be withdrawn. The displacement of any carrier into and out of an applicator or into and out of storage is performed by a flexible driving cable passing through the entrance connector of a selected active cavity.

10 Claims, 6 Drawing Figures

APPARATUS FOR STORING AND EJECTING RADIOACTIVE SOURCES USED IN RADIOTHERAPY

FIELD AND BACKGROUND OF THE INVENTION

Medical treatments by curietherapy require radioactive sources whose characteristics depend on the localization and the extent of the zone to be treated. These sources, which are placed in source carriers, are stored in an enclosure provided for this purpose and brought at the moment of treatment into a so-called projection device whereby it is enabling the introduction of these loaded source carriers into tubular applicators placed in the zone to be treated. The storage enclosure is usually placed in a room other than the treatment room, whereas the projection device is disposed next to the patient to be treated, which requires the transportation of this device and special precautions to ensure the safety of the treating staff.

In our copending application Ser. No. 788,791, filed concurrently with the present one on Apr. 19, 1977, we have disclosed and claimed details of a radioactive-source carrier guided by a flexible sheath into an applicator designed to contact an anatomical part to be treated.

OBJECT OF THE INVENTION

The object of our present invention is to provide a radiotherapeutic-treatment apparatus, usable conjointly with such applicators, adapted to store a number of source carriers and also to facilitate the ejection of one or more carriers, simultaneously or consecutively, into associated applicators.

SUMMARY OF THE INVENTION

We realize this object, in accordance with the present invention, by providing a magazine which forms a plurality of storage receptacles and at least one active receptacle each adapted to accommodate one source carrier, the combined number of active and storage receptacles exceeding the number of source carriers to be accommodated. Each active receptacle has two open ends joined via respective conduits to an entrance connector and to an exit connector positioned on the outer surface of a surrounding metallic enclosure. Also disposed on that outer surface are several ancillary connectors, one for each storage receptacle, joined to the associated receptacle by a further conduit. The exit connector of each active receptacle can be engaged by an ejection sheath, leading to a remote applicator, or to a transfer tube also attachable to an ancillary connector whereby a continuous path is formed the entrance connector of an active receptacle and the corresponding exit connector to a selected storage receptacle. With the aid of drive means engageable with a chosen source carrier, including a flexible cable insertable through the corresponding entrance connector, the various source carriers can be selectively and interchangeably fed to any applicator.

The several receptacles are, preferably, elongate cavities extending substantially axially within a metallic body of generally cylindrical shape. Advantageously, this body is surrounded by a protective screen or sleeve of a material of high atomic number, such as lead, and further by a mass of neutron-absorbing material filling an annular space between this screen and the metallic enclosure.

BRIEF DESCRIPTION OF THE DRAWINGS

The above and other features of our invention will now be described in detail with reference to the accompanying drawing in which.

SPECIFIC DESCRIPTION

Figure 1:
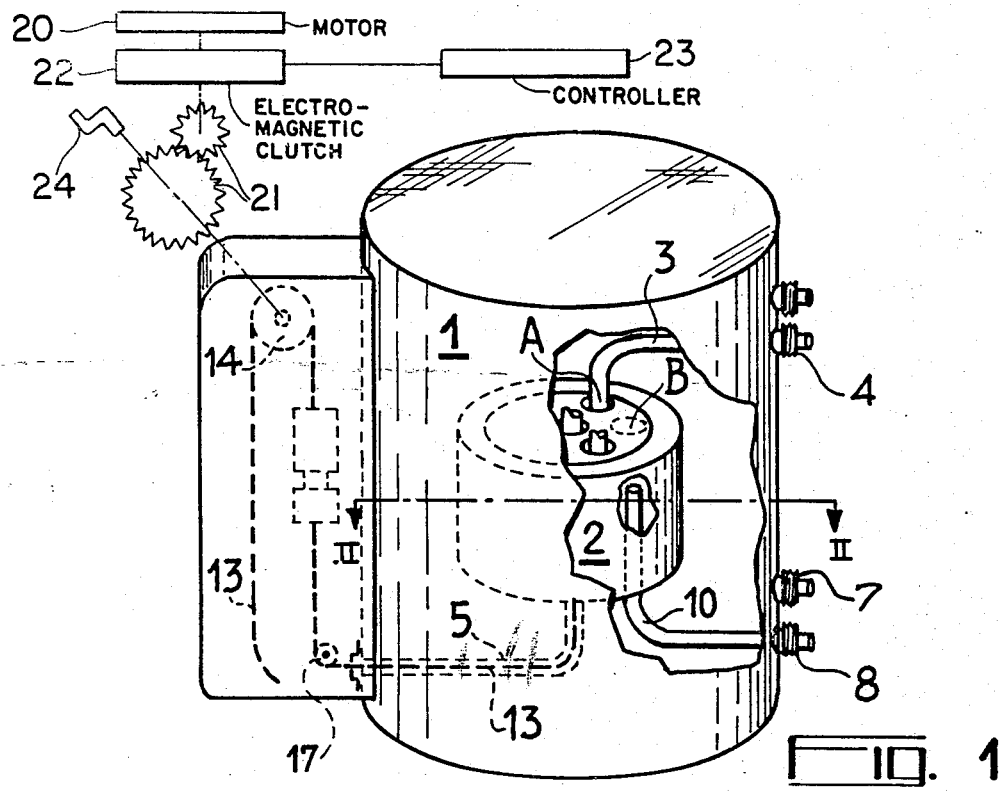
FIG. 1 is a perspective view of an apparatus embodying our invention, including a diagrammatic showing of an associated driving mechanism.
Figure 2:
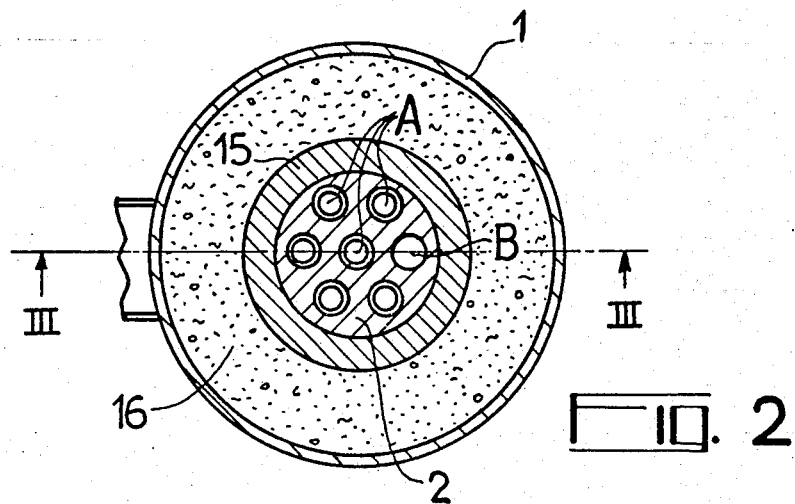
FIG. 2 is a cross-sectional view taken on the line 11—11 of FIG. 1.

A radiotherapy device according to the invention comprises, as shown in FIGS. 1 and 2, a metallic enclosure 1, for example of steel, having a cylindrical shape and containing a centrally disposed magazine 2 made, for example of stainless steel. This magazine 2 comprises n receptacles or cavities divided into p "active" cavities A and q "storage" cavities B which will be defined hereinafter. These n cavities ($p+q=n$) have a cylindrical shape and are disposed parallel to each other. They are adapted to receive ($n-1$) tubular source carriers $S_1$, $S_2$ ... which are loaded at one of their ends with a train of unitary radioactive sources. At least one of these n cavities is therefore always empty, which permits the interchange of the sources $S_1$, $S_2$ ... distributed in the different cavities A and B.

Figure 3:
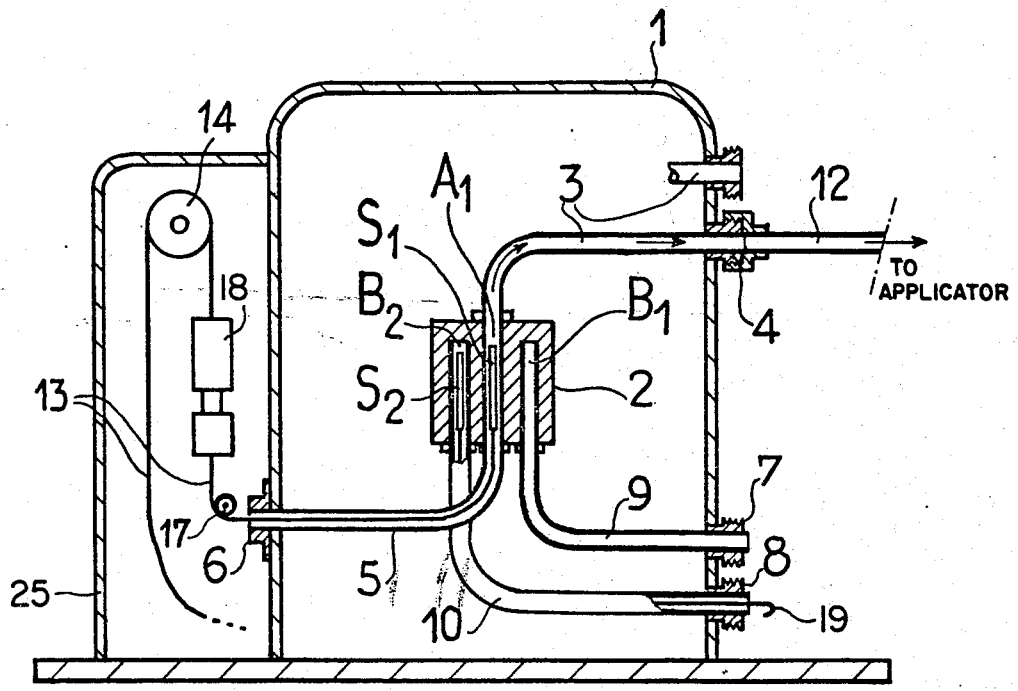
FIG. 3 is an axial sectional view taken on the line 111—111 of FIG. 2.

In FIG. 3 we have particularly illustrated an "active" cavity $A_1$ and two "storage" cavities $B_1$ and $B_2$. The open-ended cavity $A_1$ communicates at one end with a respective conduit 3 terminating at an associated exit connector 4 fixed to a wall of the enclosure 1, and at the other end with a conduit 5 terminating at an entrance connector 6 on an opposite wall of enclosure 1.

Figure 4:
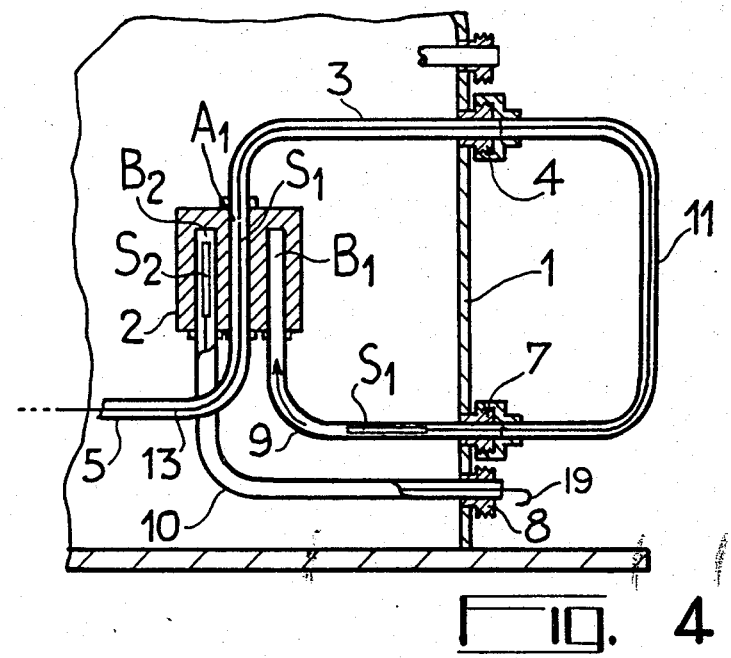
Figure 5:
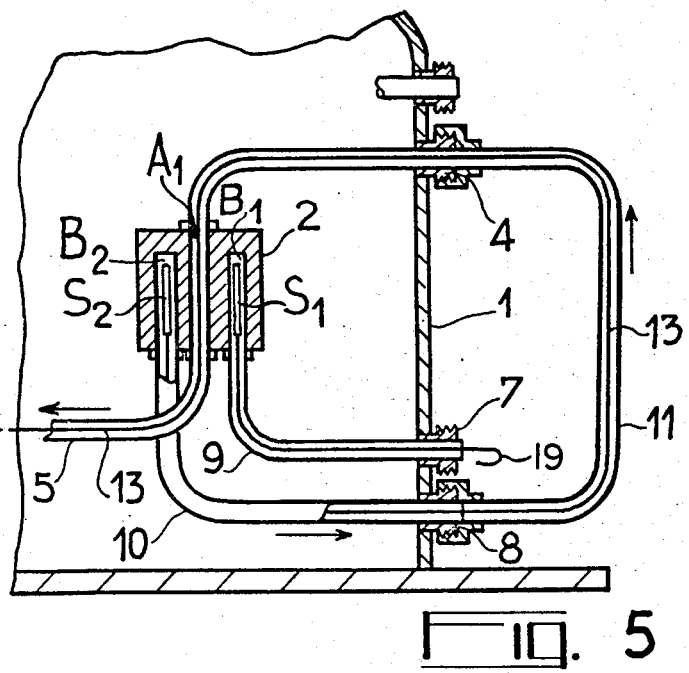

The "storage" cavities $B_1$ and $B_2$ are closed at one of their ends; their opposite ends are respectively joined to two ancillary connectors 7, 8 by conduits 9, 10. The connector 4 can be externally secured either to a sheath 12, which is to be fixed to an applicator placed in the zone to be treated, or to a transfer pipe or tube 11 as shown in FIGS. 4 and 5.

Figure 6:
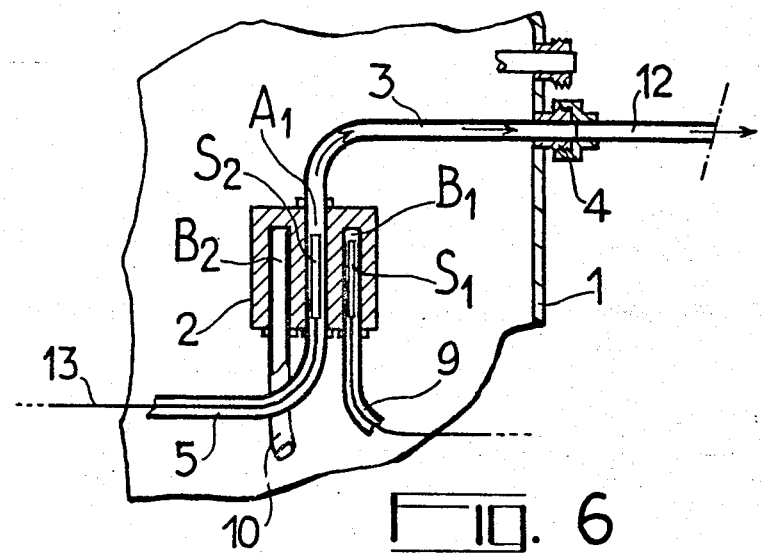
FIGS. 4–6 are fragmentary axial sectional views showing the apparatus in different phases of operation.

In operation, if it is assumed that the source carrier $S_1$ is selected for a given treatment, this carrier $S_1$, which is placed in the active cavity $A_1$, is withdrawn by a driving cable 13, entrained by a pulley 14 via a motor 20, and is projected via sheath 12 into the corresponding applicator. If it is now desired to convey the source carrier $S_2$ to this same applicator connected to the sheath 12, the replacement of the source carrier $S_1$ by the carrier $S_2$ in the active cavity $A_1$ will be carried out as shown in FIGS. 4, 5 and 6. The sheath 12 is replaced at connector 4 by the transfer pipe 11 which is also attached to the connector 7. The source carrier $S_1$ is then pushed by the driving cable 13 into the cavity $B_1$. The cable 13, disconnected from the source carrier $S_1$, is thereafter hooked to the source carrier $S_2$ (the transfer pipe 11 being now joined to the connector 8) for extraction from the cavity $B_2$ (FIG. 5) and insertion into the cavity $A_1$.

The transfer pipe 11 engaged by connector 4 is then replaced by the sheath 12 connected to the applicator.

The source carrier S₂ can thereafter be projected into this applicator (FIG. 6).

As diagrammatically illustrated in FIG. 1, motor 20 is operatively connectable with pulley 14 via a gear transmission 21 and an electromagnetic clutch 22 which is selectively actuatable by a controller 23. The controller may be preprogrammed or remote-operated. A crank 24 can be used for manually rotating the pulley 14 if the electric drive system should fail.

A housing 25, forming an extension of enclosure 1, surrounds the pulley 14 as well as guide means 18, 19 for the cable 13 which may be of the "teleflex" type. The engagement of cable 13 with a selected source carrier S₁ or S₂, for example, is facilitated by a hooked extremity 19 of that carrier.

The controller 23 may include a nonillustrated selector switch for choosing the active cavity whose clutch 22 is to be actuated. A nonillustrated safety switch may be actuated by any source carrier upon its proper positioning in the associated applicator. A further safety switch, also not shown, may indicate the return of the previously ejected source carrier to its storage cavity B.

Our improved radiotheropeutic apparatus which is both a "storer" and a "projector" of the radioactive sources placed in the carriers S₁, S₂ . . . , permits the storage of sixteen source carriers, for example, containing in all 25 μg of californium 252. The illustrated embodiment allows the simultaneous or non-simultaneous ejection of six source carriers into their respective applicators.

As seen in FIG. 2, a lead screen 15 which surrounds the magazine 2 has a thickness of a few centimeters whereas a protective mass of neutron-absorbing material 16, several tens of centimeters in thickness, fills the steel enclosure 1.

What we claim is:

1. An apparatus to be used in radiotherapy, comprising:

a metallic enclosure externally provided with at least one entrance connector, at least one exit connector and a plurality of ancillary connectors;

a plurality of radioactive-source carriers;

a magazine in said enclosure forming a plurality of storage receptacles and at least one active receptacle each adapted to accommodate a radioactive-source carrier, said active receptacle having two open ends joined via respective conduits to said entrance connector and to said exit connector, each of said storage receptacles being joined by a further conduit to a respective ancillary connector, the number of radioactive-source carriers being less than the total number of said receptacles;

a transfer tube selectively attachable to said exit connector and to any of said ancillary connectors for establishing a continuous path from said entrance connector through said active receptacle to any of said storage receptacles;

a sheath attachable in lieu of said transfer tube to said exit connector for guiding a radioactive-source carrier from said active receptacle to a remote applicator; and drive means including a flexible cable insertable through said entrance connector for selective displacement, together with an engaged radioactive-source carrier, between said active receptacle and a storage receptacle via said transfer tube or between said active receptacle and said applicator via said sheath whereby said carriers can be interchangeably fed to said applicator.

2. An apparatus as defined in claim 1 wherein said magazine is a metallic body of generally cylindrical shape, said receptacles being substantially axially extending elongate cavities in said body.

3. An apparatus as defined in claim 2, further comprising a protective screen of a material of high atomic number surrounding said body inside said enclosure.

4. An apparatus as defined in claim 3 wherein said material of high atomic number is lead.

5. An apparatus as defined in claim 3, further comprising a mass of neutron-absorbing material filling an annular space between said screen and said enclosure.

6. An apparatus as defined in claim 1 wherein said magazine includes a plurality of active receptacles each provided with its own entrance and exit connectors and an associated flexible cable, said drive means including at least one motor and control means for operatively connecting same with the flexible cable associated with a selected active receptacle.

7. An apparatus as defined in claim 6 wherein said drive means further includes a pulley engaging said flexible cable.

8. An apparatus as defined in claim 7 wherein said enclosure is provided with an external attachment surrounding said pulley and said entrance connector, further comprising guide means for said flexible cable in said attachment.

9. An apparatus as defined in claim 7 wherein said drive means further comprises a hand crank for manually operating said pulley.

10. An apparatus as defined in claim 1 wherein said radioactive-source carriers are provided with hooked extremities engageable by said flexible cable.

* * * * *